United States Patent [19]

Corral

[11] Patent Number: 5,139,517
[45] Date of Patent: Aug. 18, 1992

[54] ORTHOTOPIC INTRAVENTRICULAR HEART PUMP

[76] Inventor: David F. Corral, P. O. Box 10759, Fort Worth, Tex. 76114

[21] Appl. No.: 737,823

[22] Filed: Jul. 26, 1991

Related U.S. Application Data

[62] Division of Ser. No. 433,364, Nov. 8, 1989, abandoned.

[51] Int. Cl.$^5$ ............................................... A61M 1/10
[52] U.S. Cl. ............................................ 623/3; 600/16
[58] Field of Search ................. 623/2, 3, 900; 600/16, 600/17, 18

[56] References Cited

U.S. PATENT DOCUMENTS

| | | | |
|---|---|---|---|
| 2,982,511 | 5/1961 | Connor | 251/5 |
| 3,409,913 | 11/1968 | Kantrowitz et al. | 623/3 |
| 3,553,736 | 1/1971 | Kantrowitz et al. | 623/3 |
| 3,568,214 | 3/1971 | Goldschmied | 623/3 |
| 3,604,016 | 9/1971 | Robinson et al. | 623/3 |
| 3,668,708 | 6/1972 | Tindal | 623/3 |
| 3,827,426 | 8/1974 | Page et al. | 623/3 |
| 3,885,251 | 5/1975 | Pedroso | 623/3 |
| 4,058,855 | 11/1977 | Runge | 623/3 |
| 4,144,595 | 3/1979 | Unger | 623/3 |
| 4,195,623 | 4/1980 | Zeff et al. | 623/3 |
| 4,245,622 | 1/1981 | Hutchins, IV | 623/3 |
| 4,453,537 | 6/1984 | Spitzer | 623/3 |
| 4,536,893 | 8/1985 | Parravicini | 623/3 |
| 4,621,617 | 11/1986 | Sharma | 623/3 |
| 4,662,598 | 5/1987 | Weingarten | 251/5 |
| 4,731,076 | 3/1988 | Noon et al. | 623/2 |

FOREIGN PATENT DOCUMENTS 2112472  7/1983  United Kingdom ............... 417/394

Primary Examiner—Randy C. Shay
Attorney, Agent, or Firm—Alan W. Lintel

[57] ABSTRACT

An intraventricular pump (IVP) is a surgically-implanted orthotoxic heart pump capable of augmenting either one or both of the heart's ventricles. The IVP pumps blood using an internal diaphragm which is hydrualically activated by a physiologically-controlled pacemaker pump system. The entire system is contained within the human body and is powered by a rechargeable battery system. An artificial valve is incorporated into the right-sided IVP which is hydraulically-activated to work in conjunction with the IVP.

12 Claims, 3 Drawing Sheets

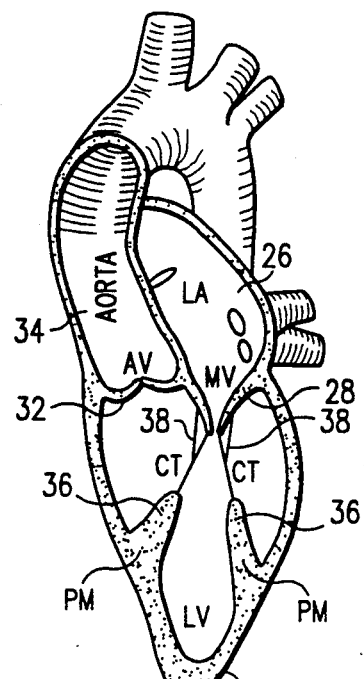
FIG. 3A
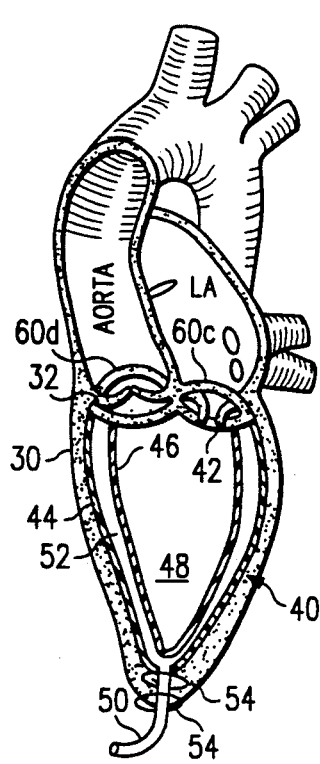
FIG. 3B
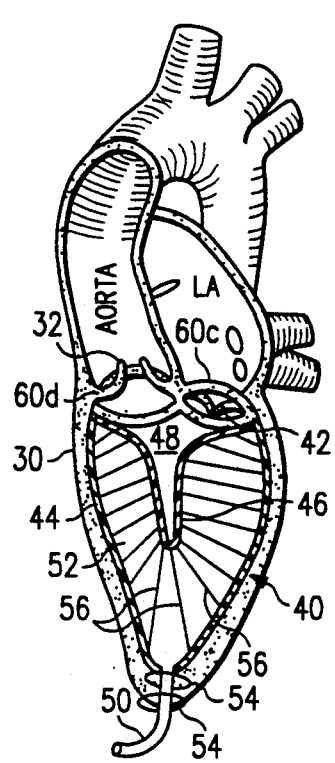
FIG. 3C
FIG. 4A
FIG. 4B
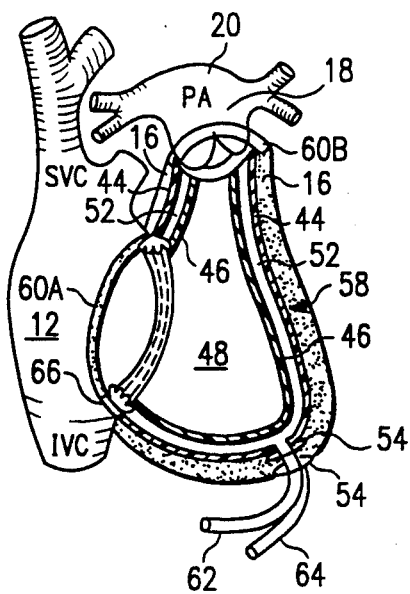

ORTHOTOPIC INTRAVENTRICULAR HEART PUMP

This is a divisional of copending application Ser. No. 07/433,364, filed on Nov. 8, 1889, now abandoned.

TECHNICAL FIELD OF THE INVENTION

This invention relates in general to prosthetic devices, and more particularly to a physiologically activated orthotoxic heart pump.

BACKGROUND OF THE INVENTION

In recent years within the field of cardiology an increasing need for an effective, low complication prosthetic heart device has arisen. The natural heart may become incapable of maintaining adequate circulation because of various disease processes, including myocardial infarction.

Over the years, a number of artificial heart devices have been introduced in an attempt to restore normal function to otherwise failing hearts. The Jarvik-7 (J-7) artificial heart is one of the most famous and enduring of the prosthetic hearts. This device is an orthotopic design, which means it completely replaces the natural heart. It utilizes a semi-spherical ventricular chamber that contains a mobile internal diaphragm used for pumping blood. The J-7 heart is powered by an external pumping system and is used as a temporary life-sustaining measure in patients awaiting donor heart transplantation.

Multiple complications have become apparent after studying patients using the J-7 for prolonged periods of time. First, blood movement within the artificial ventricle is not uniform. Dead spaces and stagnant blood flow in peripheral areas of the semi-spherical chamber allow blood clots to form. Blood clots may then embolize into the general circulation and cause secondary complications including stroke. Second, structural compromise of the J-7 on adjacent thoracic structures including vasculature and pulmonary tissue may limit its application and create new problems in certain patients. Third, because this is an orthotopic design, the recipient's heart must be completely removed in order to attach the artificial heart. The decision to use a Jarvik-7 heart is therefore irreversible until a donor heart becomes available.

A second category of heart devices exist which work in conjunction with the natural heart in place. These pump devices secondarily augment the natural heart's function without requiring its removal and are referred to as orthotopic. In a recent study published in the *New England Journal of Medicine*, Feb. 11, 1988, Vol. 318, No. 6, pp. 333-340, a orthotopic system was utilized in which twenty-nine patients were followed over a three-year period. The results of the study showed that a orthotopic system could successfully maintain patients with irreversible heart failure in lieu of an orthotopic one.

A large advantage to a orthotopic system is that the option to pursue other possible medical or surgical interventions is preserved. The orthotopic system studied in the *New England Journal of Medicine* noted an extremely low complication rate associated with embolic events. The system, however, incorporates multiple externalized blood pumping tubes and used an external pump system. The National Institute of Health is currently funding research extending from the study previously cited in the *New England Journal of Medicine*. The orthotopic heart pump has been modified to remain within the confines of the human body. The pump, referred to as a left ventricular assist device (LVAD), channels blood entering the left ventricle to a pump located in the abdomen, then back into the abdominal aorta. Another pump system currently under investigation, which may be utilized under temporary circumstances, is the Nimbus pump system. The Nimbus pump forces blood flow by a set of rotating blades from the left ventricle into the aorta. Both pumps bypass blood flow around the weak left ventricle to augment circulation.

Therefore, a need exists for an effective orthotopic prosthetic heart device capable of augmenting right, left of both ventricles. It must not compromise thoracic structures or be prone to inducing blood clots or hemolysis. Blood flow characteristics should duplicate natural circulatory patterns and the pump should be responsive to normal increases or decreases in the body's physiological demands.

The heart device should minimize the risk of accidental blood loss by augmenting blood flow within the natural confines of the circulatory system, without externalized diversion. The system should be totally contained within the human body and be capable of sustained activity away from external power sources. Simple recharging methods should allow for quick, risk-free replenishment of the system's power supply. Such a system would not only serve as an effective temporary heart pump, but could also have significant potential for long-term use.

SUMMARY OF THE INVENTION

In accordance with the present invention, a orthotopic, intraventricular pump (IVP) which is used in conjunction with the natural heart. The IVP is surgically placed within the heart's ventricular chamber and may be used to augment either right, left or both ventricles.

The IVP's semirigid outer casing is preferably formed from plastic and approximates the heart's normal diastolic ventricular dimensions. Overlying the internal surface of the IVP is a multi-layered flexible sheet of plastic material or other suitable material, that is affixed at the inlet/outlet ports. A free space exists between the inner surface of the IVP and the overlying flexible sheet. Diaphragmatic movement mimicking natural ventricular contraction occurs when hydraulic pressure is directed into the free space. Tethering cords linking the diaphragm to the IVP insure a consistent shape and provide an additional impetus for the diaphragm to recoil back to a contracted state. A remote battery-powered hydraulic pump electrically-linked to the heart's natural conductive system powers the IVP. The physiologically-responsive system is located within the abdominal cavity.

In a second embodiment of the present invention is a low-profile, artificial, hydraulically-activated heart valve. This valve is designed to replace the right ventricular tricuspid valve. The right atrium is a very low pressure area and artificial valves at this site are prone to a multitude of dysfunctional clot-related problems.

In the left ventricular IVP at the inlet/mitral valve position—a prosthetic porcine heart valve probably offers the most efficient and least complicated valvular alternative.

The artificial right-sided inlet valve is incorporated into the IVP and utilizes the same principle of diaphragmatic movement as the IVP. Tether cords linking the diaphragm to the IVP casing insure consistent shape, and provide impetus to recoil. Hydraulic pressure to the valve is supplied by a remote pump hydraulically-isolated from the IVP located within the abdominal cavity.

BRIEF DESCRIPTION OF THE DRAWINGS

For a more complete understanding of the present invention, and the advantages thereof, reference is now made to the following description taken in conjunction with the accompanying drawings, in which:

FIGS. 3a-c illustrate an embodiment of the intraventricular heart pump of the present invention for use in connection with the left ventricle;

FIGS. 4a-b illustrate an embodiment of the intraventricular heart pump of the present invention for use in connection with the right ventricle;

FIG. 5 illustrates the present invention as located in the human body.

DETAILED DESCRIPTION OF THE INVENTION

The preferred embodiment of the present invention is best understood by referring to FIGS. 1-5 of the drawings, like numerals being used for like and corresponding parts of the various drawings.

Figure 1:
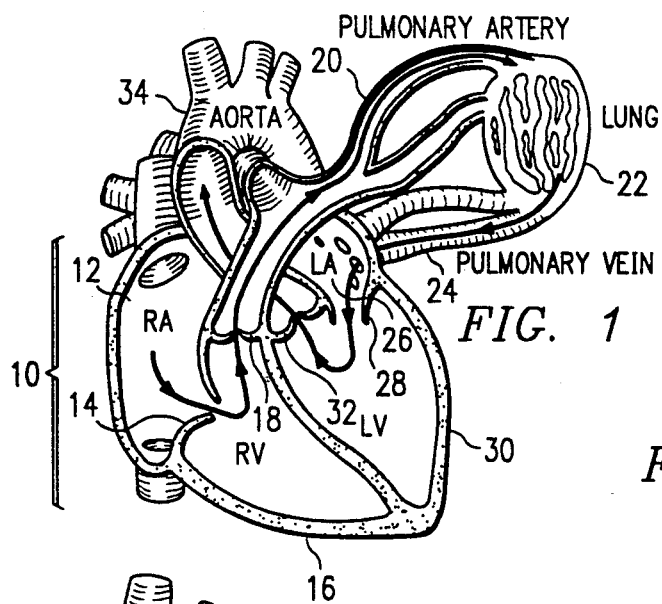
FIG. 1 illustrates blood flow in a normal heart.

In FIG. 1, the normal circulatory pattern of blood through the heart 10 is illustrated. Blood from the venous system enters the first chamber of the heart, the right atrium (R.A.) 12. From the right atrium 12, it passes through the tricuspid valve 14 into the right ventricle (R.V.) 16. Blood then exits the right ventricle 16 via the pulmonic valve 18, entering the pulmonary artery 20 which leads to the lungs 22. In the lungs 22, carbon dioxide is released and the blood is reoxygenated. Blood then exits the lungs 22, passing into the pulmonary vein 24 which leads to the left atrium (L.A.) 26. From the left atrium 26, blood passes through the mitral valve 28, into the left ventricle (L.V.) 30. Blood then exits the heart 10 via the aortic valve 32, into the aorta 34 and the generalized arterial circulation.

Cardiac contraction is orchestrated by electrical impulses originating from the heart's nervous system. Electrical stimulation to myocardial fibers results in muscular contraction. Specifically-timed electrical signals originating in the upper chambers of the heart cause the atriae to contract and empty blood into the ventricles 16 and 30. After atrial contraction, a short electrical delay takes place. This pause allows the ventricles 16 and 30 to receive blood from the atriae before they are stimulated to contract. With ventricular contraction, blood is ejected from the heart 10.

FIGS. 2a-e illustrate a simplified diagram of normal cardiac contraction as visualized from the left ventricle 30. The cardiac cycle can be broken down into two major stages: diastolic and systolic. Diastole is the relaxation phase of the ventricular contraction cycle. During this time the ventricle relaxes and fills up with blood in preparation for the next contraction. Systole is the ventricular phase involved with contraction and the process of ejecting blood from the heart.

Figure 2A:
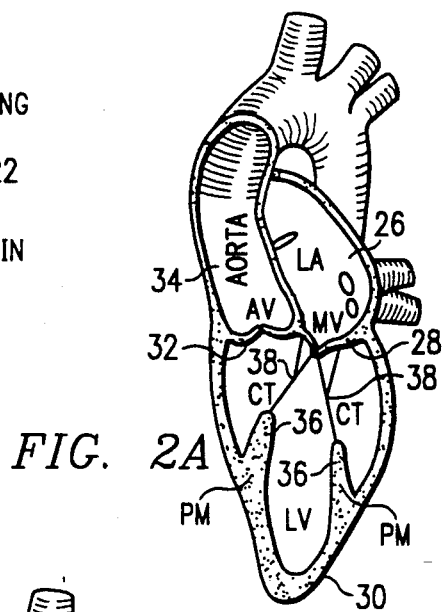
FIGS. 2a-e illustrate the pumping action of a normal heart.

FIG. 2a illustrates the first phase of diastole which is isovolumic relaxation immediately following a systolic contraction. This represents the transition phase between diastole and systole.

Figure 2B:
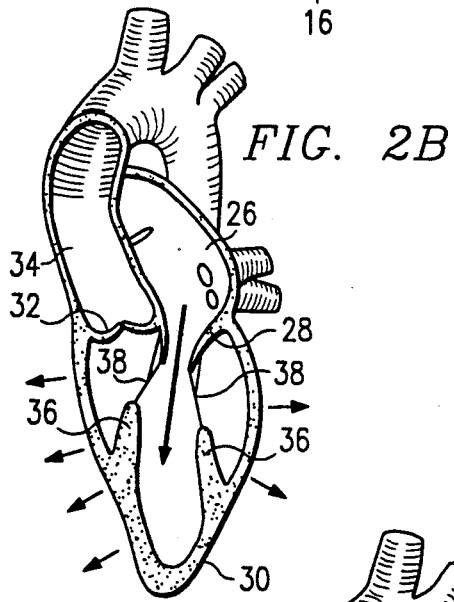

FIG. 2b illustrates that with further ventricular relaxation a building negative pressure within the ventricle due to dilation results in a rapid influx of blood. Additionally, the geometric angle formed between the ventricular wall, papillary muscle (P.M.) 36, chordae tendinae (C.T.) 38 and mitral valve (M.V.) 28 widens. This combined process results in the opening of the mitral valve 28.

Figure 2C:
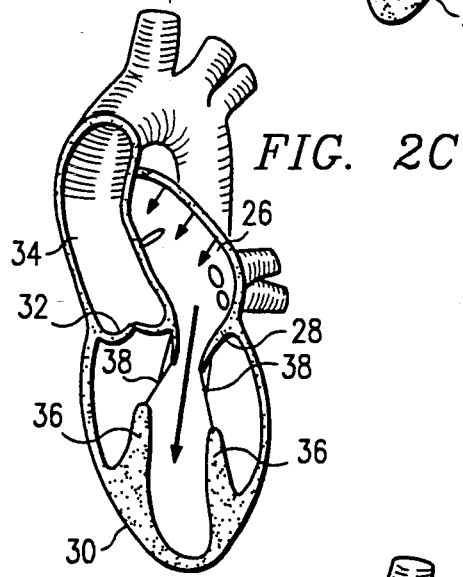

FIG. 2c illustrates the latter stages of diastolic ventricular filling. During this phase, the left atrium 26 contracts to allow for maximal ventricular filling.

Figure 2D:
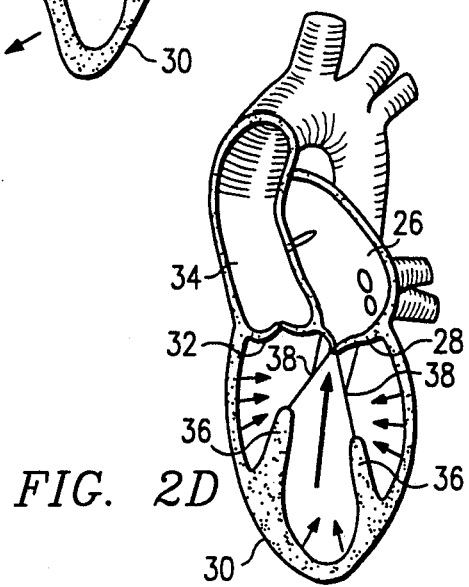

In FIG. 2d, the left ventricle 30 begins to build muscular tension prior to actually contracting and secondarily reducing ventricular volume. This phase demonstrates isovolumic contraction and is referred to as presystole. With building ventricular contraction, the intraventricular pressure increases which helps to force the mitral valve 28 closed. Additionally, the geometric relationship between the valve cusp and muscle-tendon supporting structures narrows with ventricular contraction which assists in mitral valve closure.

Figure 2E:
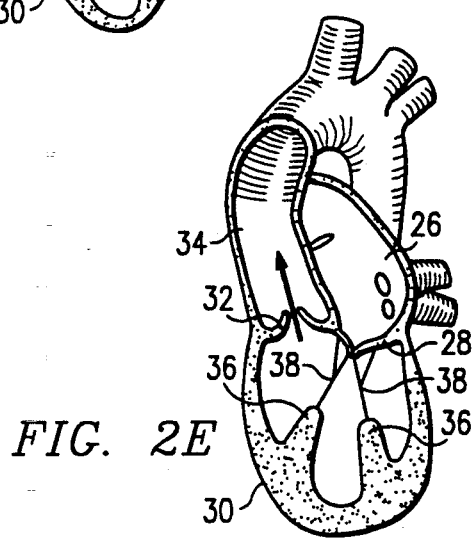

FIG. 2e illustrates that as ventricular contraction progresses, the intraventricular volume decreases and pressure builds. Once the intraventricular pressure exceeds the blood pressure within the aorta 34, the aortic valve (A.V.) 32 is pushed open. Blood is then ejected from the ventricular cavity into the aorta 34. This phase is called systole.

Cardiac transplant candidates have severely weakened hearts, incapable of maintaining adequate cardiac output. In many cases, the heart is incapable of sustaining exertional circulatory demands beyond the resting state. Various disease processes render the heart ineffective, including myocardial infarction, infiltrative diseases, extensive hypertrophy, dilation or other myopathic conditions. The end-result is a significantly weakened heart incapable of maintaining circulatory requirements, commonly referred to as heart failure.

In order to reestablish adequate circulation, many medical modalities exist. Once the heart damage/failure exceeds the ability of medical therapy to reverse it, very few options exist. At this point, mechanical augmentation or heart transplantation become the only viable options.

In an attempt to overcome the heart's inability to maintain adequate circulation, a number of augmenting devices have been introduced. The present invention is a heart augmenting device which substantially eliminates or prevents the disadvantages and problems associated with prior artificial hearts.

The intraventricular pump (IVP) may be utilized to augment either the right, left or both ventricles. FIGS. 3a-c illustrate use of the IVP 40 for the left ventricle 30.

The IVP is surgically implanted into the heart's ventricular chamber 30, which necessitates the surgical removal of the papillary muscles 36 and chordae tendinae 38. Once these residual structures are removed, the IVP 40 may be placed into the open ventricular chamber 30 (see FIG. 3b). The surgical removal of the papillary muscles 36 and chordae tendinae 38 allow for implantation of the IVP 40; however, this procedure renders the natural inlet valve inoperable.

Restoration of valvular function varies depending on which ventricular chamber is being augmented. In the left ventricle 30, a prosthetic porcine valve 42 may be utilized at the inlet position to replace the native mitral valve. The prosthetic porcine valve 42 would work in conjunction with the surgically implanted IVP 40.

In the right ventricle 16, the artificial valve is incorporated into the IVP and is hydraulically activated to open/close at appropriately-timed intervals with the IVP. This artificial valve will be discussed in more detail in connection with FIGS. 4a–b.

A cross-sectional view of the intraventricular heart pump of the present invention is illustrated in FIG. 3B (left ventricular IVP 40 in diastole) and in FIG. 4a (right ventricular IVP 58 in diastole).

The IVP's outer shell 44 is preferably semirigid and proportioned to approximate the natural shape of a normal ventricular chamber either left 30, or right 16. The right (58) and left (40) IVP's outer shell will be individually shaped to conform with the natural shape of the respective ventricle 16 or 30. The IVP's outer shell 44 sits within the natural ventricular chamber, as illustrated in FIG. 3b (left ventricle) and FIG. 4a (right ventricle). The outer shell is typically formed from semi-flexible plastics. While these materials are used in the preferred embodiment, other materials could be used without departing from the claimed invention. The diastolic volume of the IVP is tailored to the ideal predicted volume for the particular patient. The IVP thus provides a functional replacement for the heart's natural ventricle and allows for normalization of the cardiac volume despite underlying heart pathology.

The internal dimensions of the diseased ventricular chamber vary depending upon the underlying disease process. In either hypertrophied or dilated ventricles, the abnormal diastolic dimensions may debilitate inlet valve function by adversely affecting the relationship of the papillary muscle and chordae tendinae to the valve. Dysfunctional inlet valve performance may result in regurgitant, retrograde blood flow that further decreases cardiac output.

The interior of the IVP is lined by a flexible, multilayered plastic sheet that is attached to the outer shell 44 at the inlet/outlet port area. The mobile lining of the inner liner 46 comes into direct contact with inflowing blood. The inner liner 46 forms a chamber 48 which may hold blood received from the atria, either right 12 or left 26. Pumping is effected by diaphragmatic movement of the liner by applying hydraulic pressure. Pressure is introduced between the inner liner 46 and the external shell 44 (i.e., the hydraulic access chamber), which allows a circumferential, uniform compression to occur. The ventricular contraction effected by the IVP diaphragm strongly mimics the heart's natural contraction as shown in FIGS. 3c and 4b. Active movement of all diaphragmatic surfaces virtually eliminates the possibility of stagnant areas and secondary dead spaces which may lead to clots. A series of tethering cords 56 disposed between the outer shell 44 and the inner liner 46 within the hydraulic access chamber link the diaphragmatic liner 46 to the external shell 44. The cords 56 function to insure a uniform, consistent systolic ventricular shape after hydraulic pressure is applied. Once hydraulic pressure is withdrawn, the cords 56 provide an additional impetus to recoil back against the external shell 44, to a fully contracted state.

The IVP not only restores ideal diastolic ventricular volume, but further improves ventricular performance by correcting secondary inlet valve dysfunction.

Based on the underlying pathology of the diseased heart, various corrective measures may be necessary in order to surgically implant the IVP.

In hypertrophic hearts, excessive myocardium impinging on the ventricular diastolic size must be removed. This intervention will not only allow for placement of the IVP but may additionally improve outflow hemodynamics.

In dilated hearts, excessive diastolic space between the ideal-sized IVP and the enlarged ventricle may be removed by a number of methods. First, the IVP's external shell 44 can be sized to fit the enlarged ventricle and the diaphragmatic lining can be volumetrically adjusted to ideal diastolic dimension. This option would result in a larger hydraulic access chamber volume but would not require additional fluid to drive the IVP. A second possibility is to use an ideal diastolic external shell and then engineer a fit to the enlarged ventricle by placing a neutral compressible material between the IVP and ventricle.

Hydraulic fluid is transmitted to the IVP by reinforced hydraulic catheters (tubes) 50 (left IVP), 62 (right IVP) or 64 (artificial valve). The catheters travel from the hydraulic motor located in the peritoneal cavity, through the diaphragm, to the apex of the heart. At the point of entry through the apex of the heart, the catheters are covered by DACRON sheathing 54. This allows for firm surgical attachment which ultimately leads to physical incorporation. The hydraulic catheters pass through the outer shell 44, and communicate with the hydraulic access chamber 52. This allows pressure to be applied to the access chamber to activate the inner liner 46 into a systolic contraction (see FIG. 3c). A second hydraulic catheter 64 may be used in conjunction with the right ventricular IVP which allows hydraulic pressure to be transmitted to the artificial balloon valve 66 for activation (discussed later).

Once the IVP is implanted within the natural ventricular space it is secured by a number of attachment points. The outer surface of the IVP's external shell 44 sits adjacent to the ventricular wall 30 (left) or 16 (right) and is covered by DACRON. In the preferred embodiment, the IVP inlet/outlet ports are surgically secured to the heart's natural valvular orifices via DACRON cuffs. In the right ventricle 16, DACRON cuffs are used to attach the outer shell's inlet/outlet ports to the annular ring of the tricuspid valve at the right atrial area 60a and the annular ring of the pulmonary valve at the pulmonary outflow tract 60b, respectively. In the left ventricle 30, DACRON cuffs are used to attach the outer shell's inlet/outlet ports to the annular ring of the mitral valve at the left atrial area 60c, and the annular ring of the aortic valve at the aortic outflow tract 60d, respectively. DACRON is used because of its propensity to induce fibrosis, and thus become physically incorporated into adjacent tissues.

As shown in FIG. 4b, the IVP's right ventricular artificial valve 66 is a "low-profile" design incorporated into the inlet portion of the ventricular chamber 48. The multilayered plastic sheet comprising the walls of the valve may be a continuation of the IVP's inner diaphragm. The artificial valve 66 has its own separate hydraulic access chamber and hydraulic pump, completely isolated from the IVP's system. This arrangement allows both to function independently of each other. The artificial valve 66 does not utilize "expandable" materials in order to operate, rather the valve works by using the same principle of diaphragmatic motion as the IVP.

In the inactivated state, the IVP's artificial valve 66 is completely retracted back against the IVP casing. In this state (diastolic), the valve is fully opened, allowing a maximal inflow of blood. Because of the valve's ability to contract back against the walls of the inlet port lumen, it has essentially no residual structure during diastole.

This extremely low-profile means that blood flow from the atria into the ventricle is virtually unobstructed, laminar, with minimal turbulence, and therefore less prone to develop clots.

As the IVP's ventricular filling cycle progresses through diastole, the artificial valve 66 begins to activate. Activation and subsequent closure of the valve 66 occurs when increasing hydraulic pressure is applied to the hydraulic access chamber. When hydraulic fluid is forced into the valve 66, the annular-shaped diaphragm expands which closes the opening to the right atrium 12. Building hydraulic pressure forces the walls of the valve 66 toward the center of the lumen comprising the inlet area, until it ultimately seals off. Valvular closure may be timed to antedate ventricular activation to minimize regurgitation.

Figure 4C:
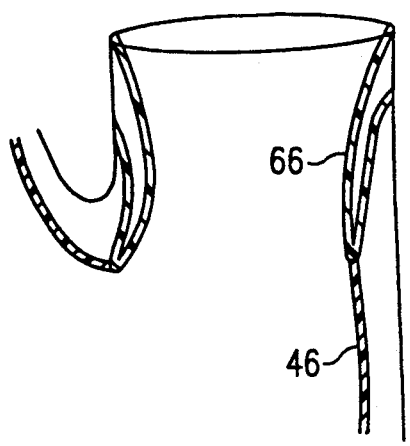
FIG. 4c illustrates the balloon valve in an open state.
Figure 4D:
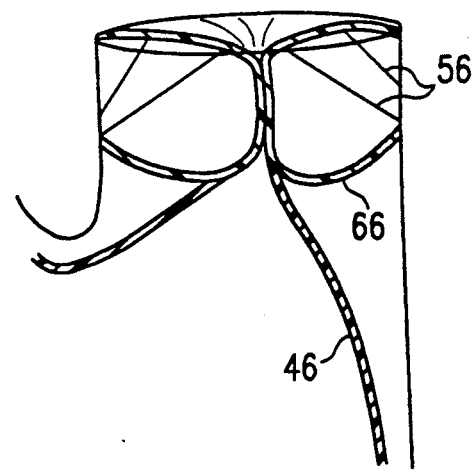
FIG. 4d illustrates the balloon valve in a closed state.
Figure 4C:
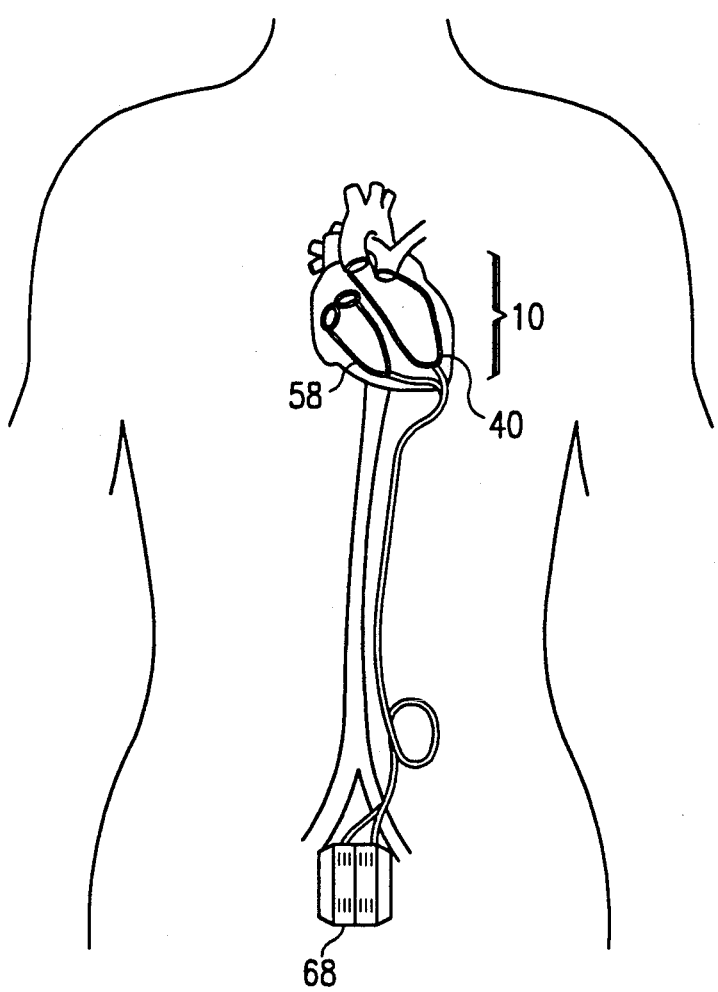

Tethering cords 56 are also used in the balloon valve 66 to shape the valve during closure and to pull the valve material back into diastolic position when the hydraulic fluid is removed. This aspect is particularly important with respect to the balloon valve 66, which must be fully opened at every cycle to allow blood to flow freely from the right atrium 12. The valve 66 is shown in FIGS. 4c-d apart from the IVP.

As shown in FIG. 3b, the left ventricular IVP's inlet valve 42 utilizes a prosthetic porcine valve. This natural valve allows blood to pass from the left atrium into the left ventricular IVP chamber 48, and functions in a manner very similar to the normal valve, based on changing ventricular pressure differentials.

As shown in FIG. 3b, the IVP is in a diastolic cycle, the prosthetic porcine valve 42 allows the passage of blood from the atrium 26 into the IVP chamber 48.

As shown in FIG. 5, the IVP is powered by a hydraulic motor system 68 which may utilize either cylinder/piston or rotary motor configurations. The rotary system is preferred because of its simplicity and paucity of moving parts, diminishing its chance for breakdown. Either system configuration would use dual hydraulic chambers. One chamber is dedicated to activating the IVP and the other to activating the artificial valve (right ventricle only).

The two hydraulic chambers (rotary or piston/cylinder) would be mechanically-linked to small electrical motors. One electric motor would drive both hydraulic chambers. A second motor is also mechanically-linked to the hydraulic chamber system, but exists in an inactive state. The function of the second motor is to serve as a backup in case of primary motor failure, insuring uninterrupted cardiac function.

An electronic pacemaker system electrically links the IVP to the heart's natural conductive system. Pacemaker wires are placed in the right atrium to detect electrical impulses originating from the sinoatrial node. The pacemaker subsequently dictates the speed of the electrical motor powering the hydraulic system. This linkage allows the IVP to be physiologically-responsive to the circulatory requirements of the body. If the natural conductive system is faulty, the pacemaker can be programmed to activate at a fixed rate.

Electrical power to operate the hydraulic system can be provided by a variety of methods. A compact, rechargeable extended-life battery or transformer system could provide DC power to the IVP. Battery systems located within the abdominal cavity could be used alone or in conjunction with other external batteries (belt) or a recharging system. Transcutaneous transmission of electrical energy through the skin to specialized sensors placed beneath the surface would eliminate the need for percutaneous, externalized power cords. Alternatively, a small electrical power cord could be externalized from inside to the outside of the body utilizing a percutaneous sheath of DACRON, with minimal infectious risk.

Although the present invention has been described in detail, it should be understood that various changes, substitutions and alterations can be made herein without departing from the spirit and scope of the invention as defined by the appended claims.

What is claimed is:

1. A method of augmenting the pumping mechanism of a heart, comprising the steps of:
    forcing hydraulic fluid into a hydraulic access chamber formed between a sac of flexible material for containing blood and an outer shell disposed within a ventricle of the heart to evacuate blood from said sac through an outlet valve of the heart; and
    removing hydraulic fluid from the hydraulic access chamber such that the sac may receive blood from an atrium.

2. The method of claim 1 wherein said forcing step comprises the step of forcing hydraulic fluid into the hydraulic chamber formed between the sac of flexible material for containing blood and the outer shell disposed within the ventricle and having cords disposed between the sac and the outer shell.

3. The method of claim 1 and further comprising the steps of:
    closing a valve disposed between the sac and the atrium prior to said step of forcing hydraulic fluid into the hydraulic access chamber; and
    opening the valve after systolic contraction, but prior to said step of removing hydraulic fluid from the hydraulic access chamber.

4. The method of claim 3 wherein said closing step comprises the step of transmitting hydraulic fluid into an expandable annular chamber disposed between the ac and the atrium.

5. The method of claim 4 wherein said opening step comprises the step of removing the hydraulic fluid from the expandable annular chamber.

6. The method of claim 4 wherein said closing step comprises the step of forcing hydraulic fluid into an expandable annular chamber having a plurality of elastic cords formed therein to maintain the annular chamber in a desired shape as hydraulic fluid is transmitted into the chamber.

7. A method of augmenting the pumping mechanism of the heart comprising the steps of:
    placing a sac formed of a flexible material and an attached outer shell into a ventricle of the heart, said sac and outer shell forming a hydraulic access chamber therebetween;

transmitting hydraulic fluid into the hydraulic access chamber to evacuate blood from said sac through an outlet chamber of the heart; and removing hydraulic fluid from the hydraulic access chamber to receive blood from an atrium into said sac.

8. The method of claim 7 and further comprising the step of maintaining a predetermined systolic shape of the hydraulic chamber.

9. The method of claim 7 wherein said maintaining step comprises the step of maintaining a predetermined systolic shape of the hydraulic chamber with a plurality of cords coupled between the sac and the outer shell.

10. The method of claim 7 and further comprising the step of selectively providing access between the sac and the atrium with a valve.

11. The method of claim 10 wherein said step of selectively providing access comprises the step of selectively providing access between the sac and the atrium with a hydraulic valve.

12. The method of claim 10 wherein said step of selectively providing access comprises the steps of:

closing the hydraulic valve prior to said transmitting step; and opening the hydraulic valve after systolic contraction, but prior to said removing step.

* * * * *